United States Patent [19]

Fischer et al.

[11] Patent Number: 4,703,117
[45] Date of Patent: * Oct. 27, 1987

[54] PROCESS FOR ISOLATING MICROBIAL POLYSACCHARIDES FROM THEIR FATTY AMINE ADDUCTS

[75] Inventors: Edgar Fischer, Frankfurt am Main; Merten Schlingmann, Königstein/Taunus, both of Fed. Rep. of Germany

[73] Assignee: Hoechst Aktiengesellschaft, Frankfurt am Main, Fed. Rep. of Germany

[*] Notice: The portion of the term of this patent subsequent to Dec. 31, 2002 has been disclaimed.

[21] Appl. No.: 783,814

[22] Filed: Oct. 7, 1985

Related U.S. Application Data

[63] Continuation of Ser. No. 522,610, Aug. 12, 1983, abandoned.

[30] Foreign Application Priority Data

Aug. 14, 1982 [DE] Fed. Rep. of Germany ....... 3230301

[51] Int. Cl.$^4$ ...................... C08B 37/00; C12P 19/04; C12P 19/06
[52] U.S. Cl. .................................... 536/114; 536/1.1; 536/127
[58] Field of Search .......................... 536/114, 1.1, 127

[56] References Cited

U.S. PATENT DOCUMENTS

| | | | |
|---|---|---|---|
| 3,422,085 | 1/1969 | Gill et al. | 536/127 |
| 3,598,730 | 8/1971 | Nordgren et al. | 536/114 |
| 3,729,460 | 4/1973 | Patton | 536/114 |
| 4,135,979 | 1/1979 | Corley et al. | 536/114 |
| 4,254,257 | 3/1981 | Schroeck | 536/114 |
| 4,562,252 | 12/1985 | Fischer et al. | 536/114 |

*Primary Examiner*—Ronald W. Griffin
*Attorney, Agent, or Firm*—Finnegan, Henderson, Farabow, Garrett & Dunner

[57] ABSTRACT

Microbial polysaccharides can be liberated from their fatty amine adducts by treating these adducts in the presence of an alcohol with a salt of ammonia or of a highly volatile amine which is soluble in this alcohol or thermally readily dissociated. It is preferable to use alcohols which have a boiling point under atmospheric pressure of up to about 100° C., and salts of ammonia or of an amine which has a boiling point of less than 150° C. under atmospheric pressure.

9 Claims, No Drawings

PROCESS FOR ISOLATING MICROBIAL POLYSACCHARIDES FROM THEIR FATTY AMINE ADDUCTS

This application is a continuation of application Ser. No. 522,610, filed Aug. 12, 1983, now abandoned.

The invention relates to a process for isolating microbial polysaccharides from their adducts with fatty amines.

Owing to their excellent properties, fermentation-produced extracellular microbial polysaccharides are used in industry as thickeners, gelling or suspending agents, protective colloids or water-binding agents. Their method of preparation makes these products rather expensive, one contributory factor to their high price being the existing, technically complicated methods of isolating them.

U.S. Pat. No. 3,928,316 discloses the isolation of the anionic heteropolysaccharide obtained by fermentation with the aid of the bacterium Xanthomonas campestris NRRL B-1459 in the form of a water-insoluble salt of a primary long-chain amine from the acidified dilute fermentation solutions. If it is intended to cleave this salt, that is done with alcoholic potassium hydroxide solution, giving the potassium salt, which, however, still contains amine.

Patent application Ser. No. 522,608 of the same date, now U.S. Pat. No. 4,591,639, issued May 27, 1986 (German Patent Application No. P 32 30 303.3) relates to a process for isolating microbial polysaccharides from their aqueous solutions by precipitating them in an acidic medium in the form of an adduct with a long-chain alkylamine, which comprises using an amine of the formula $NR^1R^2R^3$ in which $R^1$ is alkyl having 10-20 carbon atoms, and $R^2$ and $R^3$, which are identical or different, denote methyl or ethyl.

The known methods of cleaving the amine adducts do not proceed in some cases to completion, and lead to salt-containing polymers, so that it is necessary to carry out further purification operations, which are technically complicated not least because of the treatment of the effluent. The treatment of the adducts with strong alkalis can also damage the polymer.

Patent application Ser. No. 522,611 of the same date, now U.S. Pat. No. 4,562,252, issued Dec. 31, 1985 (German Patent Application No. P 32 30 302.5) relates to a process for isolating microbial polysaccharides from their amine adducts by treating them with alkaline agents in the presence of monohydric alkanols having 1 to 3 carbon atoms, which comprises using ammonia or a highly volatile amine as the alkaline agent.

In contrast, the present invention relates to a process for isolating microbial polysaccharides from their fatty amine adducts, which comprises treating these adducts in the presence of an alcohol with a salt of ammonia or of a highly volatile amine which is soluble in this alcohol or readily thermally dissociates.

Below, preferred embodiments of the invention are illustrated in more detail:

Preferable starting materials are those adducts which are derived from xanthan as the microbial polysaccharide and a primary or tertiary fatty alkylamine (having two short-chain alkyl radicals). These adducts are advantageously used in the moist state, for example in the form of a press cake, in which they are obtained in the course of isolating the microbial polysaccharides from the fermentation solutions. The drying of the adducts, which not only requires considerable amounts of energy but also can impair the solubility and swelling properties of the adducts, is thus dispensed with. The small amounts of water which are introduced when moist adducts are used do not interfere with the process according to the invention.

Suitable alcohols are in principle all those which have sufficient dissolving power for the salts mentioned or in which these salts can be readily thermally dissociated. Those alcohols are preferable which have a boiling point under atmospheric pressure of up to about 100° C., in particular lower alkanols, especially methanol, ethanol or n- or iso-propyl alcohol. The alcohols used are advantageously of the commercially available technical grade. The small amounts of water these products contain have no adverse effect on the process according to the invention. However, sizeable amounts of water are not advantageous, since the free microbial polysaccharides, in particular xanthan, are soluble in water but insoluble in alcohols. A relatively high water content in the medium could thus present a problem.

For the purposes of the invention, highly volatile amines, whose salts are used, are primarily those which boil at less than 150° C. under atmospheric pressure. Salts of amines having a higher boiling point are less advisable. For this reason, preferable salts are those of primary alkylamines having an alkyl radical of up to 6 carbon atoms, of secondary amines having identical or different alkyl radicals of up to 4 carbon atoms, and of tertiary amines having identical or different alkyl radicals of up to 3 carbon atoms. The salts of trimethylamine, triethylamine, dimethylethylamine and diethylmethylamine are particularly preferable.

Preferable salts are products which can be readily thermally dissociated, such as ammonium carbonate, ammonium formate, ammonium acetate, triethylammonium acetate, trimethylammonium formate and triethylammonium formate. In the case of more thermally stable salts it is important that they are sufficiently soluble in the alcohol at the process temperature chosen, which fact can be readily ascertained by simple preliminary experiments. Examples of useful salts are ammonium chloride, ammonium bromide, ammonium nitrate and the analogous mono-, di- and triethylammonium salts.

If the adduct of a primary or secondary fatty amine is cleaved or if the readily dissociated salt used is derived from ammonia or from a primary or secondary amine, care should be taken to ensure that the liberated amines can react with reactive groups, in particular ester groups, of the microbial polysaccharides. For this reason it is advisable in such cases to work at low to moderately elevated temperatures.

If the salts of tertiary amines are used, especially readily dissociated ones, and if adducts of tertiary amines are used, it is possible, nevertheless, to work at elevated temperatures without damaging the product. Elevated temperatures are preferable, since they considerably shorten the length of the process.

The reaction is advantageously carried out at the reflux temperature of the reaction mixture. It is possible to work under superatmospheric pressure, in particular when lower alcohols are used.

To cleave the adducts, at least an equimolar amount of salt, relative to the amine content in the adduct, is used, but it is advantageous to use a more or less sizeable excess, for example two to ten times the molar amount. Since the microbial polysaccharides liberated are insoluble in the alcoholic salt solution, excess salt, provided it remains in solution, does not interfere, since the solution can then be returned into the process. This procedure is also suitable for carrying out the process in a continuous manner.

The microbial polysaccharides are obtained in an easily separable form, and, when they have dried, they are largely in the form of the free acid. The products are distinguished by very favorable viscosity properties.

The liquid phase, which contains the alcohol and the liberated amine, can easily be worked up by distillation. The amine liberated from the adduct can immediately be used again to separate microbial polysaccharides from their fermentation solutions. The alcohol can be returned into the process.

In the Examples which follow, parts and percentages are by weight, unless otherwise indicated. Parts by volume relate to parts by weight as the liter relates to the kilogram.

First, we shall describe a method which has not been reported in the literature, whereby an adduct is prepared from xanthan and a tertiary fatty alkylamine (German Patent Application No. P 32 30 303.3):

The production strain used was Xanthomonas campestris NRRL B-1459. An agar culture in a glucose/peptone medium was transferred to the initial culture, and incubated therein at 30° C. in a shaker. This culture was used as the inoculum (3%) for a 10 liter fermenter the nutrient medium of which contained 3-5% of glucose or sucrose, 0.15-0.25% of cornsteep, 0.1 to 0.2% of sodium nitrate, 0.1% of dipotassium phosphate and 0.05% of magnesium sulfate hydrate. The inoculated fermenter was kept at 28° C., and aerated with stirring (400 rpm) at a rate of 10 liters of air/min. After about 36 hours, the fermentation medium contained 18-20 g of xanthan per liter.

0.85 g of tallowalkyldimethylamine (carbon chain distribution in the tallowalkyl radical: about 5% of $C_{14}$; 30% of $C_{16}$; and 65% of $C_{18}$) was stirred into 100 g of a xanthan solution having a polysaccharide content of 1.8%. 2.5 g of 2N acetic acid were added, the dispersion obtained was coagulated, and the adduct was precipitated in the form of initially markedly swollen flat cakes which rapidly became desolvated on further stirring. The adduct was filtered off, and washed with deionized water, and the water was removed by pressing. This gave 6.2 g of a moist press cake which contained 1.8 g of xanthan and 0.43 g of amine.

EXAMPLE 1

100 parts of a moist press cake which consists of the adduct of hexadecyldimethylamine on xanthan, which contains 32% of xanthan, were comminuted in a mixer which was equipped with a rotary cutter and held 4,000 parts of methanol, 100 parts of ammonium bromide were added, and the mixture was refluxed for 6 hours. The xanthan liberated in this process in fibrous form was filtered off, and washed with methanol until virtually bromide-free. The filter cake was dried and comminuted. The yield of xanthan was virtually guantitative (31.9 parts by weight). The product was completely soluble in deionized water.

EXAMPLE 2

Example 1 was repeated, except that a moist press cake of an adduct of hexadecylamine and xanthan, and 3,200 parts of methanol, and 100 parts of ammonium acetate were used. The xanthan obtained in a virtually quantitative yield was completely soluble in deionized water.

Examples 3-7 were carried out in a manner similar to that of Example 1, except for the modifications listed. 100 parts of adduct were used in each case. The product was always soluble in deionized water.

| Example | Xanthan adduct with | Alcohol (parts) | Salt (parts) |
|---|---|---|---|
| 3 | Coconutalkyl-dimethylamine | iso-Propyl alcohol (2,500) | Trimethylammonium acetate (170) |
| 4 | Tallowalkyl-amine | Methanol (4,000) | Ammonium formate (120) |
| 5 | Hexadecyl-amine | Methanol (3,000) | Ammonium hydrogencarbonate (80) |
| 6 | Soybeanalkyl-dimethylamine | Ethanol (3,500) | Methyldiethyl-ammonium acetate (180) |
| 7 | Tallowalkyl-dimethylamine | Methanol (3,500) | Triethylammonium chloride (200) |

We claim:

1. A process for cleaving precipitated fatty amine adducts of microbial polysaccharides containing a carboxy or ester group(s) and for isolating the free microbial polysaccharides containing a carboxy or ester group(s) from said fatty amine adducts, which comprises treating said adducts with at least an equimolar amount of a salt of ammonia or of a highly volatile amine in the presence of an alcohol in which said salt is soluble or readily thermally dissociated.

2. The process as claimed in claim 1, wherein the alcohol has a boiling point under atmospheric pressure of up to about 100° C.

3. The process as claimed in claim 1, wherein the alcohol is a lower alkanol.

4. The process as claimed in claim 1, wherein the highly volatile amine has a boiling point under atmospheric pressure of less than 150° C.

5. The process as claimed in claim 1, wherein the reaction is carried out at the reflux temperature of the reaction mixture.

6. The process as claimed in claim 1, wherein the microbial polysaccharide is xanthan.

7. The process as claimed in claim 1, wherein the fatty amine is a primary fatty alkylamine.

8. The process as claimed in claim 1, wherein the fatty amine is a tertiary fatty alkylamine which has two short-chain alkyl radicals.

9. A process for cleaving a precipitated fatty amine adduct of a xanthan polysaccharide and for isolating the free xanthan polysaccharide from said fatty amine adduct, which comprises treating said adduct with a salt of ammonia or of a highly volatile amine capable of cleaving said free xanthan polysaccharide from said fatty amine adduct in the presence of a lower alkanol in which said salt is soluble or readily thermally dissociated.

* * * * *